United States Patent [19]
Calabro et al.

[11] Patent Number: 6,049,018
[45] Date of Patent: Apr. 11, 2000

[54] SYNTHETIC POROUS CRYSTALLINE MCM-68, ITS SYNTHESIS AND USE

[75] Inventors: David C. Calabro, Princeton Junction; Jane C. Cheng, Voorhees; Robert A. Crane, Jr., Monroeville, all of N.J.; Charles T. Kresge, West Chester, Pa.; Sandeep S. Dhingra, Robbinsville, N.J.; Michael A. Steckel, Media, Pa.; David L. Stern, Mount Laurel, N.J.; Simon C. Weston, Voorhees, N.J.

[73] Assignee: Mobil Corporation, Fairfax, Va.

[21] Appl. No.: 09/234,544

[22] Filed: Jan. 21, 1999

[51] Int. Cl.[7] ............................... C01B 39/50; C07C 2/66
[52] U.S. Cl. ...................... 585/446; 585/467; 585/475; 423/706; 423/708; 423/709; 423/713; 423/718
[58] Field of Search ................... 423/706, 708, 423/713, 718, 709; 585/446, 467, 475

[56] References Cited

U.S. PATENT DOCUMENTS

| | | | |
|---|---|---|---|
| 4,511,547 | 4/1985 | Iwayama et al. | |
| 5,225,179 | 7/1993 | Zones et al. | 423/709 |
| 5,236,575 | 8/1993 | Bennett et al. | 208/46 |
| 5,501,848 | 3/1996 | Nakagawa | 423/706 |
| 5,591,421 | 1/1997 | Zones | 423/718 |

OTHER PUBLICATIONS

Schmitt, Valyocsik, and Poloski, "The role of diquaternary cations as directing agents in zeolite synthesis", Zeolite, 1994, vol. 14, 504 (No Month).

Zones, Olmstead, and Santilli, "Guest/Host Relationships in the Synthesis of Large Pore Zeolite SSZ–26 from a Propellane Quaternary Ammonium Compound", Journal American Chemical Society, 1992, vol. 114, 4195 (No Month).

www.iza–sc.ethz.ch/IZA–SC/Atlas/Table2.html (visited Dec. 12, 1999).

*Primary Examiner*—C. Melissa Koslow
*Assistant Examiner*—David Sample
*Attorney, Agent, or Firm*—Peter W. Roberts; Malcolm D. Keen

[57] ABSTRACT

This invention relates to a new synthetic porous crystalline material, designated MCM-68, a method and novel polycyclic organic cation for its preparation and its use in catalytic conversion of organic compounds. The new crystalline material exhibits a distinctive X-ray diffraction pattern and has a unique crystal structure which contains at least one channel system, in which each channel is defined by a 12-membered ring of tetrahedrally coordinated atoms, and at least two further, independent channel systems, in each of which each channel is defined by a 10-membered ring of tetrahedrally coordinated atoms, wherein the number of unique 10-membered ring channels is twice the number of 12-membered ring channels.

19 Claims, 2 Drawing Sheets

SYNTHETIC POROUS CRYSTALLINE MCM-68, ITS SYNTHESIS AND USE

BACKGROUND OF THE INVENTION

1. Field of the Invention

This invention relates to a novel synthetic porous crystalline material, to a method for its preparation and to its use in catalytic conversion of organic compounds. The invention also provides a novel organic directing agent for use in the synthesis of the crystalline material of the invention.

2. Description of the Prior Art

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline silicates. These silicates can be described as a rigid three-dimensional framework of $SiO_4$ and Periodic Table Group IIIA element oxide, e.g., $AlO_4$, in which the tetrahedra are cross-linked by the sharing of oxygen atoms whereby the ratio of the total Group IIIA element, e.g., aluminum, and silicon atoms to oxygen atoms is 1:2. The electrovalence of the tetrahedra containing the Group IIIA element, e.g., aluminum, is balanced by the inclusion in the crystal of a cation, for example an alkali metal or an alkaline earth metal cation. This can be expressed wherein the ratio of the Group IIIA element, e.g., aluminum, to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of these zeolites have come to be designated by letter or other convenient symbols, as illustrated by zeolite A (U.S. Pat. No. 2,882, 243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702,886); zeolite ZSM-11 (U.S. Pat. No. 3,709, 979); zeolite ZSM-12 (U.S. Pat. No. 3,832,449), zeolite ZSM-20 (U.S. Pat. No. 3,972,983); ZSM-35 (U.S. Pat. No. 4,016,245); zeolite ZSM-23 (U.S. Pat. No. 4,076,842); zeolite MCM-22 (U.S. Pat. No. 4,954,325); and zeolite MCM-35 (U.S. Pat. No. 4,981,663), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the $SiO_2/Al_2O_3$ ratio is at least 5 and up to the limits of present analytical measurement techniques. U.S. Pat. No. 3,941,871 (Re. 29,948) discloses a porous crystalline silicate made from a reaction mixture containing no deliberately added alumina in the starting mixture and exhibiting the X-ray diffraction pattern characteristic of ZSM-5. U.S. Pat. Nos. 4,061,724; 4,073,865 and 4,104,294 describe crystalline silicates of varying alumina and metal content.

Many zeolites are synthesized in the presence of an organic directing agent, such as an organic nitrogen compound. For example, ZSM-5 may be synthesized in the presence of tetrapropylammonium cations and zeolite MCM-22 may be synthesized in the presence of hexamethyleneimine. It is also possible to synthesize zeolites and related molecular sieves in the presence of rigid polycyclic quaternary directing agents (see, for example U.S. Pat. Nos. 5,501,848 and 5,225,179), flexible diquatemary directing agents (Zeolites, [1994], 14, 504) and rigid polycyclic diquatemary directing agents (JACS, [1992], 114, 4195).

SUMMARY OF THE INVENTION

The present invention is directed to a novel porous crystalline material, named MCM-68, a method for its preparation, and the conversion of organic compounds contacted with an active form thereof. The calcined form of the porous crystalline material of this invention possesses a very high acid activity and exhibits a high sorption capacity. MCM-68 is reproducibly synthesized by the present method in high purity.

The invention also provides a novel polycyclic organic dication useful in the synthesis of MCM-68.

DESCRIPTION OF SPECIFIC EMBODIMENTS

Figure 1:
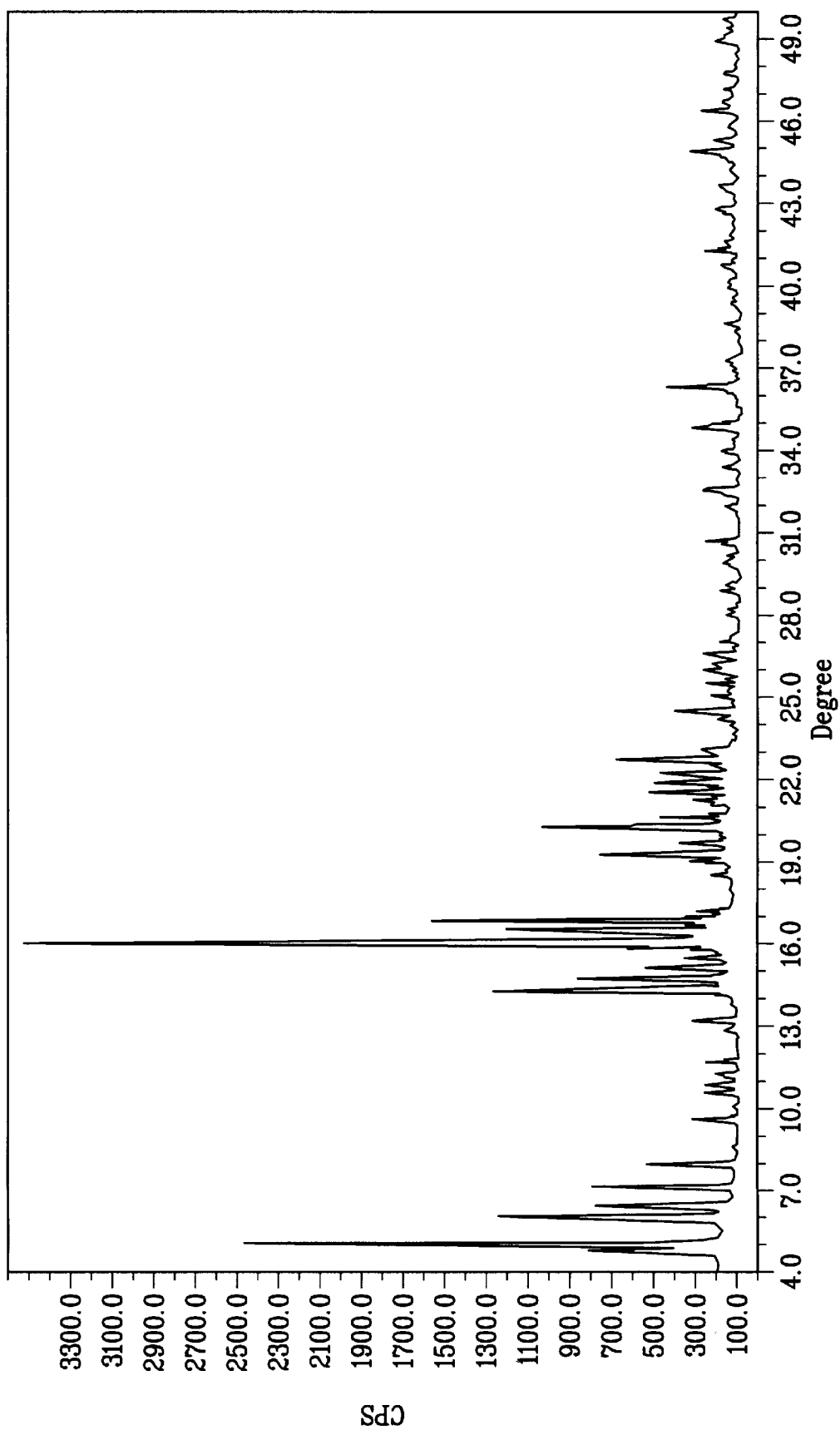
FIG. 1 shows the X-ray diffraction pattern of the as-synthesized product of Example 5.

The synthetic porous crystalline material of this invention, MCM-68, is a single crystalline phase which has a unique 3-dimensional channel system comprising at least one channel system, in which each channel is defined by a 12-membered ring of tetrahedrally coordinated atoms, and at least two further independent channel systems, in which each channel is defined by a 10-membered ring of tetrahedrally coordinated atoms, wherein the number of unique 10-membered ring channels is twice the number of 12-membered ring channels. The normal crystalline form of MCM-68 contains one 12-membered ring channel system and two 10-membered ring channel systems, in which the channels of each system extend perpendicular to the channels of the other systems and in which the 12-ring channels are generally straight and the 10-ring channels are tortuous (sinusoidal).

MCM-68 can be prepared in essentially pure form with little or no detectable impurity crystal phases and, in its calcined form, has an X-ray diffraction pattern which is distinguished from the patterns of other known as-synthesized or thermally treated crystalline materials by the lines listed in Table 1 below. In its as-synthesized form, the crystalline MCM-68 material of the invention has an X-ray diffraction pattern which is distinguished from the patterns of other known as-synthesized or thermally treated crystalline materials by the lines listed in Table 2 below.

TABLE 1

| d(Å) | Relative Intensity [100 × I/I(o)] |
|---|---|
| 13.60 +/− 0.39 | S |
| 13.00 +/− 0.37 | VS |
| 10.92 +/− 0.31 | M |
| 10.10 +/− 0.29 | M |
| 9.18 +/− 0.26 | VS |
| 8.21 +/− 0.23 | W |
| 4.58 +/− 0.13 | W |
| 4.54 +/− 0.13 | W |
| 4.45 +/− 0.13 | VW–W |
| 4.32 +/− 0.12 | VW |
| 4.22 +/− 0.12 | VW |
| 4.10 +/− 0.12 | VS |
| 4.05 +/− 0.11 | M |
| 3.94 +/− 0.11 | M |
| 3.85 +/− 0.11 | M |
| 3.80 +/− 0.11 | VW |
| 3.40 +/− 0.10 | W |
| 3.24 +/− 0.09 | W |
| 2.90 +/− 0.08 | VW |

TABLE 2

| d(Å) | Relative Intensity [100 × I/I(o)] |
|---|---|
| 13.56 +/− 0.39 | VW |
| 12.93 +/− 0.37 | M–S |
| 10.92 +/− 0.31 | W |
| 10.16 +/− 0.29 | VW–W |
| 9.15 +/− 0.26 | VW–W |
| 8.19 +/− 0.23 | VW |
| 4.58 +/− 0.13 | W |
| 4.54 +/− 0.13 | W |
| 4.44 +/− 0.12 | W |
| 4.32 +/− 0.12 | VW |
| 4.23 +/− 0.12 | VW |
| 4.10 +/− 0.12 | VS |
| 4.06 +/− 0.12 | M |
| 3.98 +/− 0.11 | W |
| 3.88 +/− 0.11 | M |
| 3.80 +/− 0.11 | VW |
| 3.40 +/− 0.10 | VW |
| 3.24 +/− 0.09 | W |
| 2.90 +/− 0.08 | VW |

These X-ray diffraction data were collected with a Scintag diffraction system, equipped with a germanium solid state detector, using copper K-alpha radiation. The diffraction data were recorded by step-scanning at 0.02 degrees of two-theta, where theta is the Bragg angle, and a counting time of 10 seconds for each step. The interplanar spacings, d's, were calculated in Angstrom units, and the relative intensities of the lines, $I/I_o$ is one-hundredth of the intensity of the strongest line, above background, were derived with the use of a profile fitting routine (or second derivative algorithm). The intensities are uncorrected for Lorentz and polarization effects. The relative intensities are given in terms of the symbols vs=very strong (80–100), s=strong (60–80), m=medium (40–60), w=weak (20–40), and vw=very weak (0–20). It should be understood that diffraction data listed for this sample as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the structure. These minor effects, including changes in relative intensities, can also occur as a result of differences in cation content, framework composition, nature and degree of pore filling, crystal size and shape, preferred orientation and thermal and/or hydrothermal history.

The crystalline material of this invention has a composition involving the molar relationship:

$$X_2O_3 : (n)YO_2,$$

wherein X is a trivalent element, such as aluminum, boron, iron, indium, and/or gallium, preferably aluminum; Y is a tetravalent element such as silicon, tin, titanium and/or germanium, preferably silicon; and n is at least about 5, such as 5 to100,000, and usually from about 8 to about 50. In the as-synthesized form, the material has a formula, on an anhydrous basis and in terms of moles of oxides per n moles of $YO_2$, as follows:

$$(0.1\text{-}2)M_2O : (0.2\text{-}2)Q : X_2O_3 : (n)YO_2$$

wherein M is an alkali or alkaline earth metal, and Q is an organic moiety. The M and Q components are associated with the material as a result of their presence during crystallization, and are easily removed by post-crystallization methods hereinafter more particularly described.

The crystalline material of the invention is thermally stable and in the calcined form exhibits a high surface area (660 m²/g with micropore volume of 0.21 cc/g) and significant hydrocarbon sorption capacity:

| | |
|---|---|
| n-Hexane sorption at 75 torr 90° C. | 10.8 Wt % |
| Benzene sorption at 75 torr 30° C. | 18.8 Wt % |
| 2,2 Dimethylbutane sorption at 60 torr 120° C. | 11.0 Wt % |
| Mesitylene sorption 2 torr at 100° C. | 3.3 Wt % |

In its active, hydrogen form MCM-68 exhibits a high acid activity, with an alpha value of 900–1000. Alpha Value is an approximate indication of the catalytic cracking activity of the catalyst compared to a standard catalyst and it gives the relative rate constant (rate of normal hexane conversion per volume of catalyst per unit time). It is based on the activity of silica-alumina cracking catalyst taken as an Alpha of 1 (Rate Constant=0.016 sec-1). The Alpha Test is described in U.S. Pat. No. 3,354,078; in the *Journal of Catalysis*, 4, 527 (1965); 6, 278 (1966); and 61, 395 (1980), each incorporated herein by reference as to that description. The experimental conditions of the test used herein include a constant temperature of 538° C. and a variable flow rate as described in detail in the *Journal of Catalysis*, 61, 395 (1980).

To the extent desired, the original sodium and/or potassium cations of the as-synthesized material can be replaced in accordance with techniques well known in the art, at least in part, by ion exchange with other cations. Preferred replacing cations include metal ions, hydrogen ions, hydrogen precursor, e.g., ammonium ions and mixtures thereof. Particularly preferred cations are those which tailor the catalytic activity for certain hydrocarbon conversion reactions. These include hydrogen, rare earth metals and metals of Groups IIA, IIIA, IVA, VA, IB, IIB, IIIB, IVB, VB, VIB, VIIB and VIII of the Periodic Table of the Elements.

When used as a catalyst, the crystalline material of the invention may be subjected to treatment to remove part or all of any organic constituent. The crystalline material can also be used as a catalyst in intimate combination with a hydrogenating component such as tungsten, vanadium, molybdenum, rhenium, nickel, cobalt, chromium, manganese, or a noble metal such as platinum or palladium where a hydrogenation-dehydrogenation function is to be performed. Such component can be in the composition by way of cocrystallization, exchanged into the composition to the extent a Group IIIA element, e.g., aluminum, is in the structure, impregnated therein or intimately physically admixed therewith. Such component can be impregnated in or on to it such as, for example, by, in the case of platinum, treating the silicate with a solution containing a platinum metal-containing ion. Thus, suitable platinum compounds for this purpose include chloroplatinic acid, platinous chloride and various compounds containing the platinum amine complex.

The above crystalline MCM-68 material can be transformed by thermal treatment. This thermal treatment is generally performed by heating at a temperature of at least about 370° C. for at least 1 minute and generally not longer than 20 hours. While subatmospheric pressure can be employed for the thermal treatment, atmospheric pressure is desired for reasons of convenience. The thermal treatment can be performed at a temperature up to about 925° C. The thermally treated product, especially in its metal, hydrogen and ammonium forms, is particularly useful in the catalysis of certain organic, e.g., hydrocarbon, conversion reactions.

The crystalline material of this invention, when employed either as an adsorbent or as a catalyst in an organic compound conversion process should be dehydrated, at least partially. This can be done by heating to a temperature in the range of 200° C. to about 370° C. in an atmosphere such as air, nitrogen, etc., and at atmospheric, subatmospheric or superatmospheric pressures for between 30 minutes and 48 hours. Dehydration can also be performed at room temperature merely by placing the MCM-68 in a vacuum, but a longer time is required to obtain a sufficient amount of dehydration.

The present crystalline material can be prepared from a reaction mixture containing sources of alkali or alkaline earth metal (M), e.g., sodium and/or potassium, cation, an oxide of trivalent element X, e.g., aluminum and/or boron, an oxide of tetravalent element Y, e.g., silicon, directing agent (Q), and water, said reaction mixture having a composition, in terms of mole ratios of oxides, within the following ranges:

| Reactants | Useful | Preferred |
|---|---|---|
| $YO_2/X_2O_3$ | at least 5 | 8–50 |
| $H_2O/YO_2$ | 10–1000 | 15–100 |
| $OH^-/YO_2$ | 0.05–2 | 0.1–0.5 |
| $M/YO_2$ | 0.05–2 | 0.1–0.5 |
| $Q/YO_2$ | 0.01–1 | 0.05–0.2 |

The organic directing agent Q used herein is selected from the novel dications N,N,N', N'-tetraalkylbicyclo[2.2.2]oct-7-ene-2,3:5,6-dipyrrolidinium dication and N,N,N',N'-tetraalkylbicyclo[2.2.2]octane-2,3:5,dipyrrolidinium dication which can be represented by the following formulae:

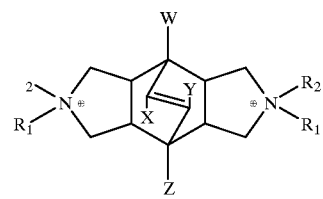

N,N,N',N'-tetraalkylbicyclo[2.2.2]oct-7-ene-2,3:5,6-dipyrrolidinium

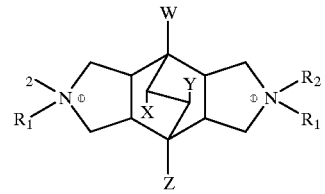

N,N,N',N'-tetraalkylbicyclo[2.2.2]octane-2,3:5,6-dipyrrolidinium where $R_1$, $R_2$ may be the same or different substituents selected from alkyl groups having 1 to 6 carbon atoms, phenyl and benzyl groups, or $R_1$ and $R_2$ may be linked as a cyclic group having 3 to 6 carbon atoms; and W, X, Y, Z may be the same or different substituents selected from hydrogen, alkyl groups having 1 to 6 carbon atoms, phenyl groups and halogens. In a preferred example, the organic directing agent is the N,N,N',N'-tetraethyl-exo exo-bicyclo[2.2.2]oct-7-ene-2,3:5,6-dipyrrolidinium (Bicyclodiquat-$Et_4$) dication, having the formula $C_{20}H_{36}N_2^{++}$, which may be represented as follows:

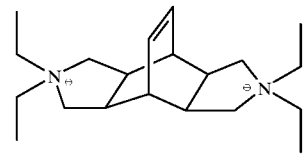

The source of the organic dication may be any salt which is not detrimental to the formation of the crystalline material of the invention, for example, the halide, e.g., iodide, or hydroxide salt.

The novel organic dications used to synthesize the MCM-8 of the invention can be prepared from, for example, exo,exo-bicyclo[2.2.2]oct-7-ene-2,3:5,6-tetracarboxylic dianhydride, which is a commercially available material. The dianhydride is initially reacted with ammonia or an amine to produce a diimide which is then reduced with $LiAlH_4$ to produce the diamine. The diamine can then be alkylated with an alkyl, phenyl or benzyl halide to produce the quaternary dication. Similarly, the bicyclooctane diquat can be produced from the dianhydride, which is known in the literature, or can be prepared by hydrogenation of the bicyclooctene dianhydride.

Crystallization of MCM-68 can be carried out at either static or stirred conditions in a suitable reactor vessel, such as for example, polypropylene jars or teflon lined or stainless steel autoclaves, at a temperature of 80° C. to about 250° C. for a time sufficient for crystallization to occur at the temperature used, e.g., from about 12 hours to about 100 days. Thereafter, the crystals are separated from the liquid and recovered.

It should be realized that the reaction mixture components can be supplied by more than one source. The reaction mixture can be prepared either batchwise or continuously. Crystal size and crystallization time of the new crystalline material will vary with the nature of the reaction mixture employed and the crystallization conditions.

Synthesis of the new crystals may be facilitated by the presence of at least 0.01 percent, preferably 0.10 percent and still more preferably 1 percent, seed crystals (based on total weight) of crystalline product.

The crystals prepared by the instant invention can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

The crystalline material of this invention can be used to catalyze a wide variety of chemical conversion processes including many of present commercial-industrial importance. Examples of chemical conversion processes which are effectively catalyzed by the crystalline material of this invention, by itself or in combination with one or more other catalytically active substances including other crystalline catalysts, include those requiring a catalyst with acid activity. Specific examples include:

(1) alkylation of aromatics with short chain ($C_2$–$C_6$) olefins, eg alkylation of benzene with ethylene or propylene to produce ethylbenzene or cumene respectively, in the gas or liquid phase, with reaction conditions including a temperature of about 10° C. to about 250° C., a pressure of about 0 to 500 psig, a total WHSV of about 0.5 $hr^{-1}$ to about 100 $hr^{-1}$, and an aromatic/olefin mole ratio of about 0.1 to about 50;

(2) alkylation of aromatics with long chain ($C_{10}$–$C_{20}$) olefins, in the gas or liquid phase, with reaction conditions including a temperature of about 250° C. to about 500° C., a pressure of about 0 to 500 psig, a total WHSV of about 0.5 $hr^{-1}$ to about 50 $hr^{-1}$, and an aromatic/olefin mole ratio of 1 to about 50;

(3) transalkylation of aromatics, in gas or liquid phase, eg transalkylation of polyethylbenzenes or polyisopropylbenzenes with benzene to produce ethylbenzene or cumene respectively, with reaction conditions including a temperature of about 100° C. to about 500° C., a pressure of about 1 to about 500 psig, and a WHSV of about $1hr^{-1}$ to about 10,000 $hr^{-1}$;

(4) disproportionation of alkylaromatics, eg disproportionation of toluene to produce xylenes, with reaction conditions including a temperature of from about 200° C. to about 760° C., a pressure of from about atmospheric to about 60 atmospheres, a weight hourly space velocity (WHSV) of about 0.1 hr–1 to about 20 $hr^{-1}$, and a hydrogen/hydrocarbon mole ratio of 0 (no added hydrogen) to about 50;

(5) dealkylation of alkylaromatics, eg deethylation of ethylbenzene, with reaction conditions including a temperature of from about 200° C. to about 760° C., a pressure of from about atmospheric to about 60 atmospheres, a weight hourly space velocity (WHSV) of about 0.1 hr–1 to about 20 $hr^{-1}$, and a hydrogen/hydrocarbon mole ratio of 0 (no added hydrogen) to about 50;

(6) isomerization of alkylaromatics, such as xylenes, with reaction conditions including a temperature of from about 200° C. to about 540° C., a pressure of from about 100 to about 7000 kPa, a weight hourly space velocity (WHSV) of about 0.1 hr–1 to about 50 $hr^{-1}$, and a hydrogen/ hydrocarbon mole ratio of 0 (no added hydrogen) to about 10;

(7) reaction of paraffins with aromatics to form alkylaromatics and light gases with reaction conditions including a temperature of about 260° C. to about 375° C., a pressure of about 0 to about 1000 psig, a WHSV of about 0.5 $hr^{-1}$ to about 10 $hr^{-1}$, and a hydrogen/hydrocarbon mole ratio of 0 (no added hydrogen) to about 10;

(8) paraffin isomerization to provide branched paraffins with reaction conditions including a temperature of about 200° C. to about 315° C., a pressure of about 100 to 1000 psig, a WHSV of about 0.5 $hr^{-1}$ to about 10 $hr^{-1}$, and a hydrogen/hydrocarbon mole ratio of about 0.5 to about 10;

(9) alkylation of iso-paraffins, such as isobutane, with olefins, with reaction conditions including a temperature of about –20° C. to about 350° C., a pressure of 0 to 700 psig, a total olefin WHSV of about 0.02 $hr^{-1}$ to about 10 $hr^{-1}$;

(10) dewaxing of paraffinic feeds with reaction conditions including a temperature of from about 200° C. to about 450° C., a pressure of about 0 to 1000 psig, a WHSV of about 0.2 $hr^{-1}$ to about 10 $hr^{-1}$, and a hydrogen/hydrocarbon mole ratio of about 0.5 to about 10; and

(11) cracking of hydrocarbons with reaction conditions including a temperature of about 300° C. to about 700° C., a pressure of about 0.1 to about 30 atmospheres, and a WHSV of about 0.1 $hr^{-1}$ to about 20 $hr^{-1}$.

(12) isomerization of olefins with reaction conditions including a temperature of about 250° C. to about 750° C., an olefin partial pressure of about 30 to about 300 kPa, and a WHSV of about 0.5 $hr^{-1}$ to about 500 $hr^{-1}$.

In the case of many catalysts, it is desired to incorporate the new crystal with another material resistant to the temperatures and other conditions employed in organic conversion processes. Such materials include active and inactive materials and synthetic or naturally occurring zeolites as well as inorganic materials such as clays, silica and/or metal oxides such as alumina. The latter may be either naturally occurring or in the form of gelatinous precipitates or gels including mixtures of silica and metal oxides. Use of a material in conjunction with the new crystal, i.e., combined therewith or present during synthesis of the new crystal, which is active, tends to change the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the new crystal include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the present crystal also include inorganic oxides, such as silica, zirconia, titania, magnesia, beryllia, alumina, and mixtures thereof.

In addition to the foregoing materials, the new crystal can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of finely divided crystalline material and inorganic oxide matrix vary widely, with the crystal content ranging from about 1 to about 90 percent by weight and more usually, particularly when the composite is prepared in the form of beads, in the range of about 2 to about 80 weight percent of the composite.

In order to more fully illustrate the nature of the invention and the manner of practicing same, the following examples are presented.

EXAMPLE 1

Synthesis of N,N'-Diethyl-exo,exo-bicyclo[2.2.2] oct-7-ene-2,3:5,6-tetracarboxylic diimide.

To a 2000-ml 3-necked round-bottomed flask equipped with a magnetic stirring bar, a reflux condenser and a thermometer were attached. The flask was then charged with 70 wt % ethylamine in water (515.25 g, 8 moles) followed by exo,exo-bicyclo[2.2.2]oct-7-ene-2,3:5,6-tetracarboxylic dianhydride (99.28 g, 0.4 moles) in portions along with vigorous stirring. After two hours of stirring at room temperature, water (300 ml) was added. The mixture was then stirred at 70° C. for 48 hours and then at 100° C. for 18 hours to drive off the excess amine. The reaction was then cooled to room temperature and the remaining ethylamine quenched with concentrated HCl in a dropwise fashion. The solid was then filtered under suction, washed with water (400 ml) and dried in a vacuum dessicator over drierite to give 120.90 g (100%) of diimide as white crystals.

Melting Point: 265–266° C.

NMR: Solvent=CDCl$_3$ $^{13}$C (δ/ppm): 12.846; 33.411; 33.776; 42.763; 130.685; 176.438.

$^1$H(δ/ppm): 1.07 (6H, t); 2.97 (4H, s); 3.47 (4H, q4); 3.78 (2H, br.s); 6.10 (2H, t).

| Combustion Analysis for $C_{16}H_{18}N_2O_4$ | | | |
|---|---|---|---|
| | % C | % H | % N |
| Calculated | 63.56 | 6.00 | 9.27 |
| Found | 63.45 | 6.00 | 9.21 |

EXAMPLE 2

Synthesis of N,N'-Diethyl-exo,exo-bicyclo[2.2.2] oct-7-ene-2,3:5,6dipyrrolidine

All glassware in this procedure was dried in an oven at 150° C. for at least 12 hours. A 2000-ml, 3-necked round-bottomed flask equipped with a magnetic stirring bar, a thermometer and a graduated pressure equalized addition funnel sealed with a septum cap was comprehensively flushed with N$_2$. To this a soxhlet extractor with a thimble containing N,N'-diethyl-exo,exo-bicyclo[2.2.2]oct-7-ene-2,3:5,6-tetracarboxylic diimide (33.26 g, 110 mmol) topped with a reflux condenser and an inline gas bubbler was attached. The system was then charged with lithium aluminum hydride powder (12.52 g, 330 mmol) and anhydrous THF (1650 ml) via the addition funnel. After 24 hours of reflux to fully extract and deliver the diimide, the reaction was cooled to 5° C. Then the reaction was quenched with water (12.5 ml), 15% NaOH solution (12.5 ml) and water (37.6 ml) keeping the temperature below 10° C. After warming to room temperature and suction filtration of the solids followed by washing with dichloromethane (660 ml), water (220 ml) was added to the combined filtrates which were then acidified using conc. HCI to pH=1-2. The organic layer was then separated, water (220 ml) added and the pH adjusted to 1-2 with concentrated HCI. This aqueous layer was separated and combined with the previous aqueous fraction, basicified with 50% NaOH solution to pH=11-12 and extracted with dichloromethane (5=275 ml). These combined organic fractions were dried over Na$_2$SO$_4$, filtered and evaporated in vacuum to give a yellow/orange oil which may solidify upon cooling (22.56 g, 83%). The oil was extracted with ether (2=150 mL), the fractions being filtered, combined, dried over Na$_2$SO$_4$, re-filtered & the solvent evaporated under vacuum to give a gold oil which solidifies upon cooling (20.15 g, 74%). $^1$H and $^{13}$C NMR analysis of the crude yellow solid showed no visible impurities and the diamine was used in this form in the subsequent diiodide preparation. However, an analytical sample of the diamine was obtained by vacuum distillation of the yellow solid (10 mTorr, 106–110° C.) to give a clear oil (52% efficiency) which crystrallizes to a white solid on cooling.

Melting Point: 57–58° C.

NMR: Solvent=CDCl$_3$ $^{13}$C (δ/ppm): 13.837; 35.491; 44.210; 49.831; 58.423; 135.294. $^1$H(δ/ppm): 1.05 (6H, t); 1.85 (4H, t); 2.37 (4H, q4); 2.49 (6H, br.d); 3.04(4H, t); 6.07 (2H, t).

| Combustion Analysis for $C_{16}H_{26}N_2$ | | | |
|---|---|---|---|
| | % C | % H | % N |
| Calculated | 77.99 | 10.64 | 11.37 |
| Found | 77.82 | 10.59 | 11.31 |

EXAMPLE 3

Synthesis of N,N,N',N'-Tetraethyl-exo,exo-bicyclo [2.2.2]oct-7-ene-2,3:5,.6-dipyrrolidinium Diiodide (Bicyclodiquat-Et$_2$ 2I)

To a 1000-mi 3-necked round-bottomed flask equipped with a magnetic stiirrng bar, a reflux condenser, a thermometer and a pressure equalized addition funnel containing a solution of iodoethane (67.37 g, 432 mmol) in ethanol (216 ml) were attached. The flask was then charged with N,N'-diethyl-exo,exo-bicyclo[2.2.21]oct-7-ene-2,3:5,6-dipyrrolidine (35.48 g, 144 mmol) and ethanol (144 ml). After stirring until all the solids had dissolved the iodoethane solution was added slowly and the mixture refluxed overnight. After subsequent cooling to 10° C., the solids were suction filtered and washed with acetone (144 ml). The resultant off-white solid was then refluxed in acetone (500 ml) for 15 minutes, suction filtered and dried in a vacuum dessicator over drierite to give a tan solid, 70.78 g (88%).

Melting Point: >270° C. (decomposition)

NMR: Solvent=D$_2$O $^{13}$C (δ/ppm): 10.115; 10.932; 35.721; 42.597; 55.604; 58.370; 67.030; 130.870.

$^1$H(δ/ppm): 1.28 (12H, t); 2.85 (8H, br.s); 2.92 (2H, br.s); 3.32 (8H, q6); 3.81 (4H, d); 6.45 (2H, t).

| Combustion Analysis for $C_{20}H_{36}N_2I_2$ | | | |
|---|---|---|---|
| | % C | % H | % N |
| Calculated | 43.02 | 6.50 | 5.02 |
| Found | 43.19 | 6.58 | 4.85 |

EXAMPLE 4

Synthesis of Aluminosilicate MCM-68

7 g of Colloidal Silica (30 wt %), Al(OH)$_3$ (Aluminum Hydroxide, solid), KOH (Potassium Hydroxide, 20 wt % solution), Bicyclodiquat-Et$_4$ 2I (N,N,N',N'-Tetraethyl-exo, exo-bicyclo[2.2.2]oct-7-ene-2,3:5,6-dipyrrolidinium diiodide, solid) and distilled water were combined in the following mole ratios:

| | |
|---|---|
| Si/Al$_2$ | 20 |
| H$_2$O/Si | 30 |
| OH/Si | 0.375 |
| K$^+$/Si | 0.375 |
| Bicyclodiquat-Et$_4$ 2I/Si | 0.10 |

The combined mixture was added to an autoclave and heated to 160° C. for 300 hours. The product was then filtered and washed with water and dried overnight under an IR lamp. The solid was subsequently calcined in air at a temperature of 540° C. for 8 hours to yield the new material designated as MCM-68. The powder pattern of the as-synthesized and calcined materials are compiled in Tables 3 and 4. The final product had trace amounts of zeolite Beta (C-56).

TABLE 3

| Two-theta | d(Å) | A/Aox100 |
|---|---|---|
| 6.54 | 13.51 | 11.4 |
| 6.85 | 12.90 | 49.1 |
| 8.11 | 10.90 | 25.0 |
| 8.71 | 10.15 | 17.2 |
| 9.68 | 9.14 | 17.6 |
| 10.82 | 8.18 | 13.2 |
| 11.66 | 7.59 | 1.4 |
| 13.01 | 6.80 | 7.0 |
| 13.69 | 6.47 | 1.3 |
| 14.36 | 6.17 | 5.2 |
| 14.76 | 6.00 | 4.9 |
| 15.17 | 5.84 | 2.8 |
| 15.31 | 5.79 | 3.9 |
| 15.92 | 5.57 | 5.4 |
| 17.46 | 5.08 | 2.1 |
| 18.01 | 4.93 | 7.4 |
| 19.39 | 4.58 | 37.6 |
| 19.55 | 4.54 | 31.1 |
| 19.98 | 4.44 | 22.6 |
| 20.56 | 4.32 | 13.1 |
| 21.02 | 4.23 | 5.9 |
| 21.73 | 4.09 | 100.0 |
| 21.87 | 4.06 | 40.0 |
| 22.37 | 3.97 | 35.1 |
| 22.90 | 3.88 | 48.5 |
| 23.40 | 3.80 | 4.0 |
| 24.41 | 3.65 | >1.0 |
| 25.16 | 3.54 | 3.4 |
| 25.38 | 3.51 | 1.1 |
| 25.84 | 3.45 | 5.9 |
| 26.20 | 3.40 | 19.0 |

TABLE 3-continued

| Two-theta | d(Å) | A/Aox100 |
|---|---|---|
| 26.76 | 3.33 | 6.9 |
| 27.56 | 3.24 | 26.6 |
| 28.08 | 3.18 | 9.9 |
| 28.74 | 3.11 | 2.6 |
| 28.91 | 3.09 | 4.4 |
| 29.23 | 3.06 | 10.9 |
| 29.66 | 3.01 | 10.1 |
| 30.15 | 2.964 | 9.5 |
| 30.57 | 2.925 | 2.9 |
| 30.85 | 2.898 | 16.3 |
| 31.33 | 2.855 | 4.7 |
| 32.09 | 2.789 | >1.0 |
| 32.50 | 2.755 | 1.0 |
| 32.87 | 2.724 | 2.7 |
| 33.23 | 2.696 | 9.0 |
| 33.97 | 2.639 | 3.5 |
| 34.30 | 2.614 | 1.5 |
| 34.58 | 2.594 | 4.7 |
| 34.86 | 2.573 | 1.7 |
| 35.32 | 2.541 | 5.0 |
| 35.58 | 2.523 | 3.5 |
| 36.07 | 2.490 | 2.4 |
| 36.75 | 2.445 | 2.2 |
| 37.00 | 2.430 | 1.8 |
| 38.09 | 2.362 | 1.7 |
| 38.33 | 2.348 | 1.6 |
| 39.31 | 2.292 | 2.6 |
| 39.65 | 2.273 | 2.4 |
| 40.78 | 2.213 | 2.4 |
| 41.23 | 2.189 | 1.1 |
| 41.78 | 2.162 | 4.5 |
| 43.62 | 2.075 | 1.9 |
| 44.43 | 2.039 | 4.8 |
| 45.62 | 1.988 | 2.3 |
| 46.42 | 1.956 | 2.4 |
| 47.00 | 1.933 | 1.1 |
| 47.65 | 1.908 | 5.8 |
| 49.68 | 1.835 | 7.7 |

TABLE 4

| Two-theta | d(Å) | A/Aox100 |
|---|---|---|
| 6.50 | 13.61 | 61.7 |
| 6.79 | 13.01 | 100.0 |
| 8.08 | 10.94 | 51.1 |
| 8.73 | 10.12 | 43.9 |
| 9.62 | 9.19 | 85.3 |
| 10.76 | 8.22 | 33.3 |
| 11.08 | 7.99 | 12.7 |
| 13.01 | 6.81 | 5.7 |
| 13.63 | 6.49 | 17.3 |
| 13.98 | 6.33 | 1.9 |
| 14.32 | 6.19 | 2.1 |
| 14.81 | 5.98 | 7.6 |
| 15.87 | 5.58 | 6.3 |
| 17.42 | 5.09 | 6.9 |
| 17.60 | 5.04 | 3.3 |
| 17.96 | 4.94 | 3.5 |
| 19.34 | 4.59 | 25.5 |
| 19.53 | 4.54 | 25.7 |
| 19.94 | 4.45 | 19.3 |
| 20.52 | 4.33 | 10.3 |
| 20.98 | 4.23 | 6.4 |
| 21.65 | 4.11 | 85.0 |
| 21.89 | 4.06 | 54.6 |
| 22.52 | 3.95 | 49.4 |
| 23.05 | 3.86 | 55.5 |
| 23.39 | 3.80 | 12.5 |
| 24.71 | 3.60 | 2.5 |
| 25.12 | 3.55 | 4.1 |
| 25.85 | 3.45 | 6.1 |
| 26.13 | 3.41 | 21.1 |
| 26.45 | 3.37 | 5.1 |

TABLE 4-continued

| Two-theta | d(Å) | A/Aox100 |
|---|---|---|
| 26.89 | 3.32 | 9.9 |
| 27.48 | 3.25 | 32.4 |
| 27.67 | 3.22 | 14.5 |
| 28.16 | 3.17 | 11.5 |
| 28.68 | 3.11 | 5.0 |
| 28.89 | 3.09 | 5.7 |
| 29.19 | 3.06 | 16.4 |
| 29.60 | 3.02 | 7.6 |
| 29.88 | 2.990 | 7.4 |
| 30.27 | 2.953 | 14.0 |
| 30.81 | 2.902 | 15.3 |
| 31.38 | 2.851 | 10.0 |
| 32.07 | 2.790 | 1.3 |
| 32.45 | 2.759 | >1.0 |
| 32.98 | 2.716 | 2.6 |
| 33.33 | 2.688 | 8.2 |
| 33.98 | 2.638 | 2.9 |
| 34.53 | 2.597 | 4.8 |
| 34.84 | 2.575 | 1.7 |
| 35.28 | 2.544 | 2.0 |
| 35.66 | 2.518 | 5.1 |
| 36.18 | 2.483 | 3.8 |
| 36.79 | 2.443 | 1.8 |
| 37.32 | 2.409 | 1.0 |
| 38.21 | 2.355 | 2.3 |
| 38.57 | 2.334 | 0.9 |
| 39.30 | 2.293 | 2.1 |
| 39.72 | 2.269 | 1.7 |
| 40.66 | 2.219 | 1.0 |
| 41.11 | 2.195 | 1.5 |
| 41.43 | 2.179 | 1.8 |
| 41.78 | 2.162 | 4.5 |
| 43.44 | 2.083 | 1.0 |
| 43.74 | 2.069 | 1.9 |
| 44.28 | 2.046 | 1.4 |
| 44.87 | 2.020 | 5.2 |
| 45.55 | 1.991 | 1.6 |
| 46.63 | 1.948 | 2.0 |
| 46.95 | 1.935 | 1.0 |
| 47.65 | 1.908 | 4.8 |
| 48.00 | 1.895 | 3.3 |
| 49.67 | 1.835 | 5.3 |

EXAMPLE 5

Synthesis of Aluminosilicate MCM-68.

14 g of Colloidal Silica Sol (30 wt % of $SiO_2$: Aldrich Ludox SM-30),and 22.096 g of distilled water are mixed with 0.6056g of $Al(OH)_3$ (Aluminum Hydroxide, solid). To this reaction mixture added 7.354g of KOH (88.8% purity) (Potassium Hydroxide, 20 wt % solution) and then added 3.912g of Bicyclodiqaut-$Et_4$ 2I (N,N,N',N'-Tetraethyl-exo, exo-bicyclo[2.2.2]oct-7-ene-2,3:5,6-dipyrrolidinium diiodide, solid). The reaction can be represented by the following mole ratios:

| | |
|---|---|
| Si/$Al_2$ | 18 |
| $H_2O$/Si | 30 |
| OH/Si | 0.375 |
| $K^+$/Si | 0.375 |
| Bicyclodiquat-$Et_4$ 2I/Si | 0.10 |

Figure 2:
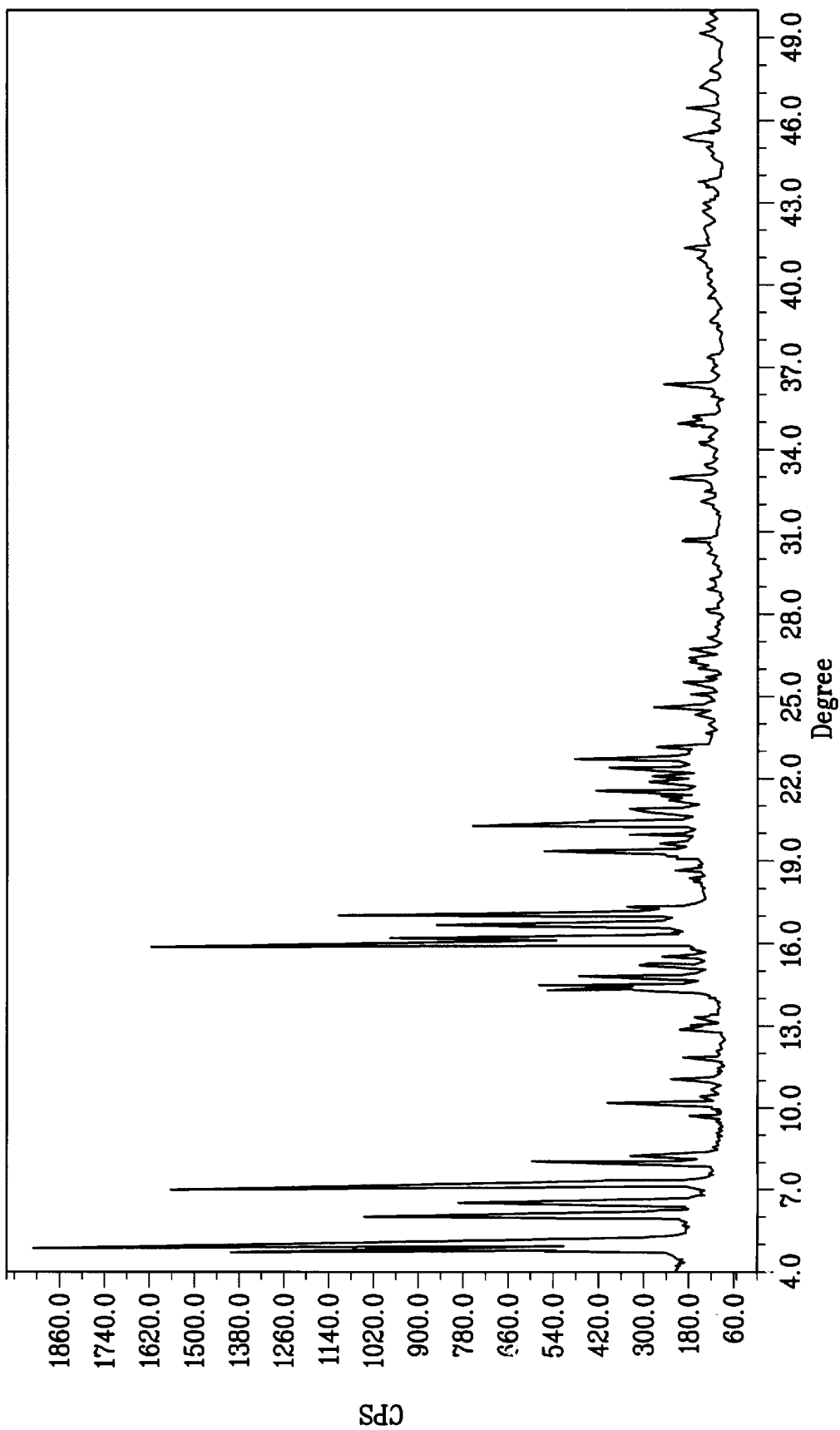
FIG. 2 shows the X-ray diffraction pattern of the as-calcined product of Example 5.

The combined mixture was added to an autoclave and heated to 160° C. for 300 hours unstirred. The product was then filtered and washed with water and dried overnight under an IR lamp. The solid is subsequently calcined in air at a temperature of 540° C. for 8 hours to yield the new material designated as MCM-68. The powder diffraction peaks for the as-synthesized and calcined samples collected using a synchrotron source are shown in FIGS. 1 and 2.

EXAMPLE 6

Ammonium Exchange and Preparation of H-MCM-68

The calcined MCM-68 material from Example 5 was ion exchanged 4 four times with a 1M ammonium nitrate solution at 80° C. then filtered washed and dried under an IR lamp. Subsequently it was calcined at 540° C. in air for 8 hrs. The H-MCM-68 obtained had an alpha value of a 1000.

EXAMPLE 7

Synthesis of Aluminosilicate MCM-68

7 g of Colloidal Silica (30 wt %), $Al(OH)_3$ (Aluminum Hydroxide, solid), KOH (Potassium Hydroxide, 20 wt % solution), Bicyclodiqaut-$Et_4$ 2I (N,N,N',N'-Tetraethyl-exo, exo-bicyclo[2.2.2]oct-7-ene-2,3:5,6-dipyrrolidinium dilodide, solid) and distilled water were combined in the following mole ratios:

| | |
|---|---|
| Si/$Al_2$ | 30 |
| $H_2O$/Si | 30 |
| OH/Si | 0.375 |
| $K^+$/Si | 0.375 |
| Bicyclodiquat-$Et_4$ 2I/Si | 0.10 |

The combined mixture was added to an autoclave and heated to 160° C. for 150 hours. The product was then filtered and washed with water and dried overnight under an IR lamp. The solid was subsequently calcined in air at a temperature of 540° C. for 8 hours to yield the new material designated as MCM-68. The powder x-ray diffraction the final product had trace amounts of zeolite ZSM-12.

EXAMPLE 8

Synthesis of Aluminosilicate MCM-68

7 g of Colloidal Silica (30 wt %), $Al(OH)_3$ (Aluminum Hydroxide, solid), KOH (Potassium Hydroxide, 20 wt % solution), Bicyclodiqaut-$Et_4$ 2 1 (N,N,N',N'-Tetraethyl-exo, exo-25 bicyclo[2.2.2]oct-7-ene-2,3:5,6-dipyrrolidinium diiodide, solid) and distilled water were combined in the following mole ratios:

| | |
|---|---|
| Si/$Al_2$ | 15 |
| $H_2O$/Si | 30 |
| OH/Si | 0.375 |
| $K^+$/Si | 0.375 |
| Bicyclodiquat-$Et_4$ 2I/Si | 0.10 |

The combined mixture was added to an autoclave and heated to 160° C for 240 hours. The product was then filtered and washed with water and dried overnight under an IR lamp. The solid was subsequently calcined in air at a temperature of 540° C. for 8 hours to yield the new material designated as MCM-68. The powder x-ray diffraction the final product had trace amounts of zeolite Beta.

EXAMPLE 9

Synthesis of Aluminosilicate MCM-68

14 g of Colloidal Silica (30 wt %), $Al(OH)_3$ (Aluminum Hydroxide, solid), KOH (Potassium Hydroxide, 20 wt % solution), Bicyclodiqaut-Et$_4$ 2I (N,N,N',N'-Tetraethyl-exo, exo-bicyclo[2.2.2]oct-7-ene-2,3:5,6-dipyrrolidinium diiodide, solid) and distilled water were combined in the following mole ratios:

| | |
|---|---|
| Si/Al$_2$ | 18 |
| H$_2$O/Si | 30 |
| OH/Si | 0.375 |
| K$^+$/Si | 0.375 |
| Bicyclodiquat-Et$_4$ 2I/Si | 0.10 |

The combined mixture was added to an autoclave and heated to 170° C. for 200 hours at 200 rpm. The product was then filtered and washed with water and dried overnight under an IR lamp. The solid was subsequently calcined in air at a temperature of 540° C. for 8 hours to yield the new material designated as MCM-68.

EXAMPLE 10

Synthesis of Aluminosilicate MCM-68 with 2 wt. % seeds of as-synthesized MCM-68.

7 g of Colloidal Silica (30 wt %), Al(OH)$_3$ (Aluminum Hydroxide, solid), KOH (Potassium Hydroxide, 20 wt % solution), Bicyclodiqaut-Et$_4$ 2I (N,N,N',N'-Tetraethyl-exo, exo-bicyclo[2.2.2]oct-7-ene-2,3:5,6-dipyrrolidinium diiodide, solid) and distilled water were combined in the following mole ratios:

| | |
|---|---|
| Si/Al$_2$ | 18 |
| H$_2$O/Si | 30 |
| OH/Si | 0.375 |
| K$^+$/Si | 0.375 |
| Bicyclodiquat-Et$_4$ 2I/Si | 0.10 |

To this mixture were added 2 wt. % seed crystals of as-synthesized MCM-68 from Example 5. The combined mixture was added to an autoclave and heated to 160° C. for 200 hours. The product was then filtered and washed with water and dried overnight under an IR lamp. The solid was subsequently calcined in air at a temperature of 540° C. for 8 hours to yield the new material designated as MCM-68.

EXAMPLE 11

Synthesis of Aluminosilicate MCM-68 with 5 wt. % Seeds of As-synthesized MCM-68.

280 g of Colloidal Silica (30 wt %), Al(OH)$_3$ (Aluminum Hydroxide, solid), KOH (Potassium Hydroxide, 20 wt % solution), Bicyclodiqaut-Et$_4$ 2I (N,N,N',N'-Tetraethyl-exo, exo-bicyclo[2.2.2]oct-7-ene-2,3:5,6-dipyrrolidinium diiodide, solid) and distilled water were combined in the following mole ratios:

| | |
|---|---|
| Si/Al$_2$ | 18 |
| H$_2$O/Si | 30 |
| OH/Si | 0.375 |
| K$^+$/Si | 0.375 |
| Bicyclodiquat-Et$_4$ 2I/Si | 0.10 |

To this mixture were added 5 wt.% seed crystals of as-synthesized MCM-68 from Example 5. The combined mixture was added to an autoclave and heated to 160° C. for 200 hours. The product was then filtered and washed with water and dried overnight under an IR lamp. The solid was subsequently calcined in air at a temperature of 540° C. for 8 hours to yield the new material designated as MCM-68.

EXAMPLE 12

Synthesis of Ti-MCM-68

7 g of Colloidal Silica (30 wt %), Al(OH)$_3$ (Aluminum Hydroxide, solid), KOH (Potassium Hydroxide, 20 wt % solution), Bicyclodiqaut-Et$_4$ 2I (N,N,N',N'-Tetraethyl-exo, exo-bicyclo[2.2.2]oct-7-ene-2,3:5,6-dipyrrolidinium diiodide, solid), Ti(OMe)$_4$ (Titanium Methoxide) and distilled water are combined in the following mole ratios:

| | |
|---|---|
| Si/Al$_2$ | 18 |
| H$_2$O/Si | 30 |
| OH/Si | 0.375 |
| K$^+$/Si | 0.375 |
| Bicyclodiquat-Et$_4$ 2I/Si | 0.10 |
| Ti/Si | 0.05 |

The combined mixture is added to an autoclave and heated to 160° C. for 200 hours.

The product is then filtered and washed with water and dried overnight under an IR lamp. The solid is subsequently calcined in air at a temperature of 540° C. for 8 hours to yield Ti-MCM-68.

EXAMPLE 13

Use of MCM-68 in Ethylbenzene Conversion

The calcined H-MCM-68 material from Example 6 was used to effect conversion of a 50wt % ethylbenzene/50 wt % xylene feed at temperatures of 350° C. and 400° C., a WHSV of 10, a hydrogen to hydrocarbon mole ratio of 3, atmospheric pressure and the results after 4 hours on stream are summarized in Table 5 below.

TABLE 5

| | Temperature, deg. C. | |
|---|---|---|
| % yield (feed basis) | 350 | 400 |
| benzene | 6.5 | 7.5 |
| toluene | 9.3 | 9.4 |
| o-xylene | 7.8 | 8.6 |
| m-xylene | 18.9 | 19.6 |
| p-xylene | 8.3 | 8.8 |
| ethylbenzene | 24.6 | 24.9 |
| MEB | 7.1 | 6.1 |
| DMEB | 3.5 | 3.7 |
| DEB | 6.2 | 4.4 |
| TMB | 2.6 | 2.5 |
| % ethylbenzene conversion | 51.3 | 50.9 |
| % xylene conversion | 31.1 | 27.6 |
| % ethyl loss | 14 | 20.7 |
| % methyl loss | 12.3 | 9.6 |
| % selectivity to xylene disproportionation | 31.9 | 35 |
| MEB/DMEB* | 2.3 | 1.86 |

*MEB = methylethylbenzene, DMEB = dimethylethylbenzene, DEB = diethylbenzene, TMB = trimethylbenzene The ethylbenzene conversion and ethyl loss results In Table 5 demonstrate that, under the conditions used, MCM-68 is highly active for the acid-catalysed delkylation of ethylbenzene.

EXAMPLE 14

Use of MCM-68 in Liquid Phase Ethylation of Benzene

H-MCM-68 crystal, as prepared in Example 6, was pelletized and sized to 14–30 mesh particles. 0.25 gram of the sized catalyst was diluted with sand to 3 cc and charged to an isothermal, down-flow, fixed-bed, $\frac{3}{8}$" outside diameter reactor. The catalyst was dried at 125° C. and atmospheric pressure with 100 cc/min of flowing nitrogen for 2 hours. The nitrogen supply was turned off and benzene (chemical grade) was fed into the reactor at 60 cc/hr for 1 hr and then at 6.4 cc/hr while the reactor temperature and pressure were increased to 200° C. and 500 psig, respectively. After the desired temperature and pressure were reached, ethylene (Matheson CP grade) was introduced from a mass flow controller at 2 WHSV (4 benzenelethylene molar ratio) and the temperature was adjusted to 220° C. After lining out, liquid products were collected in a cold-trap and analyzed off-line with a HP 5890 GC equipped with a DB-1 capillary column. Ethylene conversion was determined by measuring unreacted ethylene relative to feed ethylene. Data for MCM-68 are shown in Table 6 and demonstrate that MCM-68 is highly active and selective for the ethylation of benzene to produce ethylbenzene.

TABLE 6

| Catalyst | MCM-68 |
| --- | --- |
| Ethylene WHSV, hr$^{-1}$ | 2.0 |
| Days on stream | 0.8 |
| Ethylene conversion, % | 98.0 |
| Product Distribution | |
| Ethylbenzene | 88.393 |
| Diethylbenzene | 10.468 |
| Triethylbenzene | 0.595 |
| Tetraethylbenzene | 0.116 |
| Sum of Alkylation Products | 99.572 |
| Lights | 0.000 |
| Xylenes and styrene | 0.000 |
| C$_9$ aromatics | 0.035 |
| Butylbenzene | 0.254 |
| Sec-Butylethylbenzene | 0.045 |
| Diphenylethane | 0.094 |
| Others | 0.000 |
| Sum of By-Products | 0.428 |

EXAMPLE 15

Use of MCM-68 in Polyethylbenzene/benzene Transalkylation 0.5 gram of 14–30 mesh H-MCM-68 from Example 6 was diluted with sand to 3 cc and charged to an isothermal, down-flow, fixed-bed, $\frac{3}{8}$" outside diameter reactor. After drying the catalyst under nitrogen as described in Example 14, the reactor pressure was increased to 500 psig. A feed containing 75.03 wt % benzene, 21.74 wt % diethylbenzene, 0.92 wt % butylbenzene, and 1.02 wt % triethylbenzene was introduced into the reactor at 60 cc/hr for 1 hour and then reduced to 5 WHSV while the reactor temperature was ramped to 220° C. at 5° C./min. After lining out, liquid products were collected and analyzed off-line as described in Example 14. Catalyst performance is shown in Table 7 which demonstrates that MCM-68 is an active and selective catalyst for the production of ethylbenzene by the transalkylation of polyethylenezenes with benzene.

TABLE 7

| Catalyst | MCM-68 |
| --- | --- |
| Temperature, ° C. | 220 |
| Days on stream | 1.1 |
| Diethylbenzene conversion, % | 41.4 |
| Butylbenzene conversion, % | 21.8 |
| Product Distribution | |
| Lights | 0.797 |
| Toluene | 0.041 |
| Ethylbenzene | 98.243 |
| Xylenes and styrene | 0.000 |
| Cumene | 0.025 |
| n-Propylbenzene | 0.008 |
| Others | 0.888 |

EXAMPLE 16

Liquid Phase Cumene Synthesis Via Benzene Propylation

One gram 14–30 mesh H-MCM-68 from Example 6 was diluted with sand to 3 cc and charged to an isothermal, down-flow, fixed-bed, $\frac{3}{8}$" outside diameter reactor. The catalyst was dried as in Example 14 and benzene (chemical grade) was fed into the reactor at 60 cc/hr for 1 hr and then reduced to 6.4 cc/hr while the reactor pressure was increased to 300 psig. Propylene (Matheson CP grade) was introduced from a syringe pump at 0.5 WHSV (6 benzenelpropylene molar ratio). Temperature was adjusted to 130° C. and after lining out, liquid products were collected and analyzed as in Example 14. Propylene conversion was determined by measuring unreacted propylene relative to feed propylene. Total material balances were typically 100±2%. Data for MCM-68 are shown in Table 8 and demonstrate that MCM-68 is highly selective for the production of cumene by propylation of benzene.

TABLE 8

| Catalyst | MCM-68 |
| --- | --- |
| Propylene WHSV, hr$^{-1}$ | 1.0 |
| Days on stream | 9.8 |
| Propylene conversion, % | 99.97 |
| Product Distribution | |
| Cumene | 90.597 |
| Diisopropylbenzene | 5.973 |
| Other C$_{12}$ Aromatics | 0.638 |
| C$_{15}$ Aromatics | 1.385 |
| Sum of Alkylation Products | 98.593 |
| Propylene oligomers | 1.172 |
| C$_8$ Aromatics | 0.235 |
| n-Propylbenzene | 0.000 |
| Others | 0.000 |
| Sum of By-Products | 1.407 |

EXAMPLE 17

Liquid Phase Cumene Synthesis Via Diisopropylbenzene/benzene Transalkylation One gram of 14–30 mesh H-MCM-68 from Example 6 was diluted with sand to 3 cc and charged to an isothermal, down-flow, fixed-bed, $\frac{3}{8}$" outside diameter reactor. The catalyst was dried as in Example 14 and the reactor pressure was increased to 300 psig. The feed (75.0 wt. % benzene, 16.7 wt. % m-diisopropylbenzene and 8.3 wt % p-diisopropylbenzene) was fed into the reactor at 60 cc/hr for 1 hour and then at 4 total WHSV. The reactor temperature was ramped to 1 80° C. at 5° C./min. After lining out, liquid products were collected and analyzed off-line as in Example 14. Catalyst performance is shown in Table 9, which demonstrates that MCM-68 is an active and selective catalyst for the production of cumene by the transalkylation of diisopropylbenzene with benzene.

TABLE 9

| Catalyst | MCM-68 |
| --- | --- |
| Temperature, ° C. | 180 |
| Days on stream | 4.9 |
| Diisopropylbenzene conversion, % | 56.9 |
| Product Distribution | |
| Lights | 0.048 |
| Toluene | 0.015 |
| Ethylbenzene | 0.200 |
| Xylenes and styrene | 0.000 |
| Cumene | 99.583 |
| n-Propylbenzene | 0.061 |
| Triisopropylbenzene | 0.000 |
| Others | 0.094 |

EXAMPLE 18-Toluene Disproportionation

The general procedure described in Examples 14–17 was followed but the feed used was toluene which had been percolated over activated alumina and the conditions included a temperature of 806° F., a pressure of 300 psig, a WHSV of 6, and $H_2$/HC (molar) of 1. The results are summarized in Table 10 below:

TABLE 10

| Yields (wt. %) | |
| --- | --- |
| $C_5^-$ | 0.3 |
| Benzene | 14.4 |
| Ethylbenzene | 0.3 |
| Para Xylene | 4.5 |
| Meta Xylene | 9.7 |
| Ortho Xylene | 4.3 |
| Total $C_9^+$ | 7.6 |
| Toluene Conversion (%) | 41.0 |
| Total Xylenes Yield | 18.4 |
| Para Selectivity | 24.2 |
| Benzene/Xylene Molar | 1.06 |

The high TDP activity evident in the above results is consistent with the high alpha activity of the catalyst.

EXAMPLE 19

Ethylbenzene Conversion and Xylene Isomerization Over 0.5% Re/MCM-68

1.5 g of H-MCM-68 produced in Example 6 was steamed at 990° F. for 3 hours (in 100% steam) and was then impregnated with 0.5 wt. % Re via incipient wetness impregnation by adding a solution of 0.015 g of perrhenic acid solution in water (50% contained Re by weight) and 0.35 g of additional water, dropwise, to the steamed zeolite. The catalyst was then dried at 120° C. for 2 hours and calcined at 350° C. for 2 hours in flowing air. The resultant catalyst was loaded with sand as packing material into the reactor used in Examples 14–18 and was then heated to 350° C. under nitrogen. Hydrogen was introduced, and the catalyst reduced at 350° C. for one hour under flowing hydrogen. Following this, the reaction conditions were adjusted as indicated in Table 11 and a mixed $C_8$ feed was introduced into the reactor. Sample analyses were acquired via on-line GC analyses and the results are summarized in Table 11.

TABLE 11

| Temp. (° F.) | | 669 |
| --- | --- | --- |
| Pressure (psig) | | 204 |
| WHSV (1/Hr) | | 10 |
| $H_2$/HC (molar) | | 2 |
| Yields (wt. %) | Feed | Product |
| $C_5^-$ | | 0.1 |
| Benzene | | 1.4 |
| Toluene | | 12.6 |
| Ethylbenzene | 10.4 | 4.3 |
| Para Xylene | 1.1 | 15.0 |
| Meta Xylene | 63.4 | 34.3 |
| Ortho Xylene | 25.1 | 14.4 |
| Total $C_9^+$ | | 18.0 |
| Ethylbenzene Conversion (%) | | 58.9 |
| Xylene Loss | | 29.0 |
| Toluene + C9 + Make | | 30.6 |
| Benzene Purity | | 100.0 |
| Para Approach (PATE) | | 99.5 |

Table 11 shows that 0.5% Re on MCM-68 converts ethylbenzene, and that it also isomerizes xylenes to equilibrium. The low temperature required for these reactions is consistent with an extremely active catalyst.

What is claimed is:

1. A synthetic porous crystalline material which contains at least one channel system, in which each channel is defined by a 12-membered ring of tetrahedrally coordinated atoms, and at least two further, independent channel systems, in each of which each channel is defined by a 10-membered ring of tetrahedrally coordinated atoms, wherein the number of unique 10-membered ring channels is twice the number of 12-membered ring channels.

2. The crystalline material of claim 1 which contains one 12-membered ring channel system and two 10-membered ring channel systems.

3. The crystalline material of claim 2 in which the channels in each 10-membered ring channel system extend in a direction generally perpendicular to the channels in the other 10-membered ring channel system and to the channels in the 12-membered ring channel system.

4. The crystalline material of claim 2 in which the 12-ring channels are generally straight and the 10-ring channels are tortuous.

5. A synthetic porous crystalline material characterized by an X-ray diffraction pattern including d-spacing and relative intensity values substantially as set forth in Table 1 of the specification and having a composition comprising the molar relationship $$X_2O_3\!:\!(n)YO_2,$$

wherein n is at least about 5, X is a trivalent element, and Y is a tetravalent element.

6. The crystalline material of claim 5 having a composition, on an anhydrous basis and in terms of moles of oxides per n moles of $YO_2$, expressed by the formula:

$$(0.1\text{-}2)M_2O\!:\!(0.2\text{-}2)Q\!:\ X_2O_3\!:\!(n)YO_2$$

wherein M is alkali or alkaline earth metal and Q is an organic moiety.

7. The crystalline material of claim 6 wherein said Q comprises a dication selected from a N,N,N',N'-tetraalkylbicyclo[2.2.2]oct-7-ene-2,3:5,6dipyrrolidinium dication and a N,N,N',N'-tetraalkylbicyclo[2.2.2]octane-2,3:5,6-dipyrrolidinium dication.

8. The crystalline material of claim 1 wherein X is a trivalent element selected from the group consisting of boron, iron, indium, gallium, aluminum, and a combination thereof; and Y is a tetravalent element selected from the group consisting of silicon, tin, titanium, germanium, and a combination thereof.

9. The crystalline material of claim 1 wherein X comprises aluminum and Y comprises silicon.

10. A method for synthesizing crystalline material exhibiting a characteristic X-ray diffraction pattern including d-spacing and relative intensity values shown in Table 1 which comprises (i) preparing a mixture capable of forming said material, said mixture comprising sources of alkali or alkaline earth metal (M), an oxide of trivalent element (X), an oxide of tetravalent element (Y), water, and directing agent (Q) comprising a dication selected from a N,N,N',N'-tetraalkylbicyclo[2.2.2]oct-7-ene-2,3:5,6-dipyrrolidinium dication and a N,N,N',N'-tetraalkylbicyclo[2.2.2]octane-2,3:5,6-dipyrrolidinium dication, and having a composition, in terms of mole ratios, within the following ranges:

| | |
|---|---|
| $YO_2/X_2O_3$ | at least 5 |
| $H_2O/YO_2$ | 10–1000 |
| $OH^-/YO_2$ | 0.05–2 |
| $M/YO_2$ | 0.05–2 |
| $Q/YO_2$ | 0.01–1 |

(ii) maintaining said mixture under sufficient conditions including a temperature of from about 80° C. to about 250° C. until crystals of said material are formed; and (iii) recovering said crystalline material from step (ii).

11. The method of claim 10 wherein said mixture has the following composition ranges:

| | |
|---|---|
| $YO_2/X_2O_3$ | 8–50 |
| $H_2O/YO_2$ | 15–100 |
| $OH^-/YO_2$ | 0.1–0.5 |
| $M/YO_2$ | 0.1–0.5 |
| $Q/YO_2$ | 0.05–0.2 |

12. The method of claim 10 wherein said mixture further comprises seed crystals in sufficient amount to enhance synthesis of said crystalline material.

13. The method of claim 10 wherein X comprises aluminum and Y comprises silicon.

14. A process for converting a feedstock comprising organic compounds to conversion product which comprises contacting said feedstock at organic compound conversion conditions with a catalyst comprising an active form of the synthetic porous crystalline material of claim 5.

15. The process of claim 14 wherein the organic compound is an aromatic hydrocarbon and the process is alkylation.

16. The process of claim 15 wherein the aromatic hydrocarbon is benzene and the process includes alkylating the benzene with an olefin selected from ethylene and propylene.

17. The process of claim 14 wherein the organic compound is an alkylaromatic hydrocarbon and the process is transalkylation.

18. The process of claim 17 wherein the process includes transalkylating an alkylaromatic hydrocarbon selected from polyethylbenzenes and polyisopropylbenzenes with benzene.

19. The process of claim 14 wherein the organic compound is an alkylaromatic hydrocarbon and the process is selected from isomerization, disproportionation and dealkylation.

* * * * *

UNITED STATES PATENT AND TRADEMARK OFFICE
CERTIFICATE OF CORRECTION

PATENT NO. : 6,049,018
DATED : April 11, 2000
INVENTOR(S) : David C. Calabro et al.

It is certified that error appears in the above-identified patent and that said Letters Patent is hereby corrected as shown below:

Column 2,
Lines 15, and 17, "diquatemary" should be -- diquaternary --.

Column 4,
Line 36, "Alpha Value" should be -- Alpha value --.

Column 6,
Lines 5 and 15, in the formula "$_2$" should be -- $R_2$ --.
Line 29, "exo exo" should be -- exo,exo --.
Line 47, "MCM-8" should be -- MCM-68 --.

Column 7,
Lines 51, 58, and 65, "hr-1" should be -- $hr^{-1}$ --.

Column 9,
Line 37, "CDCI$_3$" should be -- $CDCl_3$ --.
Line 55, "6dipyrrolidine" should be -- 6-dipyrrolidine --.

Column 10,
Lines 9 and 11, "HCl" should be -- HC1 --.
Line 14, "(5=275)" should be -- (5x275) --.
Line 18, "(2=150)" should be -- (2x150) --.
Line 29, "CDCI$_3$" should be -- $CDCl_3$ --.
Line 45, "2,3:5,.6" should be -- 2,3:5,6 --.
Line 46, "Bicyclodiquat-Et$_4$ 2I" should be -- Bicyclodiquat-Et$_2$ 2I --.
Line 48, "1000-mi" should be -- 1000-ml --.
Line 49, "stiirring" should be -- stirring --.

Column 11,
Line 16, "Bicyclodiquat-Et$_4$2I" should be -- Bicyclodiquat-Et$_2$ 2I --.

Column 13,
Line 50, "Bicyclodiquat-Et$_4$ 2I" should be -- Bicyclodiquat-Et$_2$ 2I --.

Column 14,
Lines 18, and 43, "Bicyclodiquat-Et$_4$ 2I" should be -- Bicyclodiquat-Et$_2$ 2I --.
Line 44, "exo-25 bicyclo" should be -- exo-bicyclo --.

UNITED STATES PATENT AND TRADEMARK OFFICE
CERTIFICATE OF CORRECTION

PATENT NO. : 6,049,018
DATED : April 11, 2000
INVENTOR(S) : David C. Calabro et al.

It is certified that error appears in the above-identified patent and that said Letters Patent is hereby corrected as shown below:

Column 15,
Lines 1, 27, and 54, "Bicyclodiquat-$Et_4$ 2I" should be -- Bicyclodiquat-$Et_2$ 2I --.

Column 16,
Line 12, "Bicyclodiquat-$Et_4$ 2I" should be -- Bicyclodiquat-$Et_2$ 2I --.

Column 18,
Line 29, "benzenelpropylene" should be -- benzene/propylene --.

Column 19,
Line 4, "1 80°C" should be -- 180°C --.

Column 21, claim 7,
Line 3, "2,3:5,6dipyrrolidinium" should be -- 2,3:5,6-dipyrrolidinium --.

Signed and Sealed this

Fourth Day of December, 2001

*Attest:*

*Attesting Officer*

NICHOLAS P. GODICI
*Acting Director of the United States Patent and Trademark Office*